United States Patent [19]
Spears

[11] Patent Number: 5,958,377
[45] Date of Patent: Sep. 28, 1999

[54] METHODS OF DELIVERING GASES TO GAS-DEPLETED ENVIRONMENTS

[75] Inventor: J. Richard Spears, Bloomfield Hills, Mich.

[73] Assignee: Wayne State University, Detroit, Mich.

[21] Appl. No.: 08/889,635

[22] Filed: Jul. 8, 1997

Related U.S. Application Data

[62] Division of application No. 08/730,517, Oct. 11, 1996.

[51] Int. Cl.$^6$ .......................... A61K 9/107; A61K 9/127
[52] U.S. Cl. .............................. 424/43; 424/455; 514/937
[58] Field of Search ..................... 424/455, 490, 424/489, 43; 514/937, 938, 939, 944

[56] References Cited

U.S. PATENT DOCUMENTS

| | | |
|---|---|---|
| 4,366,169 | 12/1982 | White ...................................... 424/285 |
| 4,664,680 | 5/1987 | Weber . |
| 4,677,100 | 6/1987 | Nakagawa et al. ..................... 514/202 |
| 4,865,836 | 9/1989 | Long, Jr. . |
| 4,874,509 | 10/1989 | Bullock . |
| 4,927,623 | 5/1990 | Long, Jr. . |
| 4,965,022 | 10/1990 | Litz . |
| 4,973,558 | 11/1990 | Wilson et al. . |
| 5,061,484 | 10/1991 | Heldebrant . |
| 5,080,885 | 1/1992 | Long, Jr. . |
| 5,086,620 | 2/1992 | Spears ...................................... 62/51.1 |
| 5,261,875 | 11/1993 | Spears . |
| 5,344,393 | 9/1994 | Roth et al. . |
| 5,393,513 | 2/1995 | Long, Jr. . |
| 5,407,425 | 4/1995 | Werner et al. .............................. 604/4 |
| 5,407,426 | 4/1995 | Spears . |
| 5,438,041 | 8/1995 | Zheng et al. . |
| 5,527,962 | 6/1996 | Pavia et al. . |

*Primary Examiner*—Donna C. Wortman
*Assistant Examiner*—Brenda G. Brumback
*Attorney, Agent, or Firm*—Fletcher, Yoder & Van Someren

[57] ABSTRACT

The present invention provides a method of delivering an emulsion or suspension containing a supersaturated gas into a gas-depleted environment. The method generally comprises the steps of preparing an emulsion or suspension, exposing the emulsion or suspension to a gas at a pressure greater than 2 bar, and delivering the emulsion or suspension to a gas-depleted environment at ambient pressure.

28 Claims, No Drawings

METHODS OF DELIVERING GASES TO GAS-DEPLETED ENVIRONMENTS

CROSS REFERENCE TO RELATED APPLICATIONS

This application is a divisional of application Ser. No. 08/730,517, filed Oct. 11, 1996, now pending.

TECHNICAL FIELD

This invention relates to a method for preparing a gas-supersaturated emulsion or suspension and delivering it from a high pressure environment to a gas-depleted site without the immediate onset of cavitation or bubbling.

BACKGROUND ART

The maximum concentration of gas achievable in a liquid is governed by Henry's Law. The relatively low solubility at ambient pressure of many gases (for example, oxygen or nitrogen) within a liquid such as water results in a low concentration of the gas in the liquid when these are mixed. There are, however, many applications where it would be advantageous to employ a gas in a liquid mixture where the concentration of the gas within the liquid greatly exceeds its solubility at ambient pressure.

High-pressure compression of a liquid within a liquid emulsion or solid within a liquid suspension can be used to achieve a higher dissolved gas concentration, but disturbance of this gas supersaturated liquid through ejection into a 1 bar environment from the high pressure reservoir will generally result in cavitation inception at or near the exit port. The rapid evolution of bubbles produced at the exit port vents much of the gas from the liquid, so that the high degree of gas concentration within the liquid is considerably reduced at the ambient pressures outside the high pressure vessel. Additionally, the presence of bubbles in the effluent generates turbulence and impedes the flow of the effluent beyond the exit port.

A wide variety of applications would benefit from ejection of a gas-supersaturated fluid from a high pressure reservoir into an ambient pressure environment in a manner which does not involve cavitation inception at or near the exit port. For example, organic material and plant waste streams—e.g., paper mills and chemical plants—often require an increase in dissolved oxygen content before these streams can be safely discharged into a body of water. U.S. Pat. No. 4,965,022 recognizes that a similar need may also occur at municipal waste treatment plants and that fish farms require increased dissolved oxygen levels to satisfy the needs of high density aquaculture. Other applications are disclosed in U.S. Pat. No. 5,261,875.

There are many prior art references which disclose methods of enriching the oxygen content of water. For example, U.S. Pat. No. 4,664,680 discloses several conventional types of apparatus that can be used for continuously contacting liquid and oxygen-containing gas streams to effect oxygen absorption within the liquid. Specifically, pressurizable confined flow passageways are used to avoid premature liberation of the dissolved oxygen before it is incorporated within the fluid. Other oxygen saturation devices are disclosed in U.S. Pat. Nos. 4,874,509 and 4,973,558. However, these techniques leave unsolved the problem of how to eject the gas-enriched fluid solutions from a high pressure reservoir into a lower pressure environment without the formation of bubbles in the effluent at or near the exit port.

In a previous application, Ser. No. 08/581,019, filed Jan. 3, 1996, I describe a method for ejection of gas-supersaturated liquids from a high pressure to a low pressure environment without cavitation, consisting of extrusion of the fluid through capillary channels and compression to remove cavitation nuclei along the inner surface of the channels. Hydrostatic compression at pressures between 0.5 kbar and 1.0 kbar rapidly removes cavitation nuclei and bubbles from the liquid. When a gas source is used to both pressurize the liquid and achieve a desired concentration of a relatively insoluble gas in the liquid, it is generally necessary to maintain the gas pressure in the 10 bar to 150 bar range.

The complete absence of cavitation inception in water saturated with oxygen at high concentrations permits its in vivo infusion into either venous or arterial blood for the purpose of increasing the oxygen concentration of the blood while avoiding the formation of bubbles which tend to occlude capillaries.

In contrast to this capillary channel technique, the present invention dispenses with the necessity of compressing fluids within capillary channels, relying instead on use of gas-supersaturated emulsions and suspensions.

SUMMARY OF THE INVENTION

A method is described for the use of emulsions or suspensions to transport a gas-supersaturated liquid from a high pressure reservoir to a relatively low pressure environment (including ambient pressure), without immediate cavitation inception.

If a liquid that has a relatively high gas solubility (also known as the internal phase) is suspended in fine droplets within another immiscible liquid or semi-solid having a relatively low gas solubility (known as the carrier or external phase) a high level of supersaturation of the gas can be achieved in the resulting emulsion upon its release to a gas-depleted environment at ambient pressure. Likewise, solid particles can be suspended within a liquid carrier to form a suspension with the same properties (unless otherwise indicated, the descriptions for liquid in liquid emulsions are true for solid in liquid suspensions as well). The primary gases of interest for the formation of gas supersaturated emulsions are oxygen, nitrogen, and carbon dioxide.

The small size of the droplets or particles in conjunction with exposure to a transient high hydrostatic pressure confers stability to the droplets or particles in a manner similar to that provided by small diameter capillary tubes. Generally, the fine droplets are between about 0.1 micron and about 10 microns in diameter. Thus, after release of the emulsion to an ambient pressure environment, the gas that is dissolved at high levels of supersaturation will not form bubbles, despite a relatively high concentration of the gas within the droplets or particles.

The carrier of the droplets or particles is stable at high gas partial pressures because of the relatively low gas solubility of the carrier as well as the absence of gas nuclei after hydrostatic compression. A low gas diffusion coefficient in the carrier results in a slow, delayed release of the gas both from the droplets or particles to the carrier as well as from the emulsion to the gas-depleted environment. Despite this slow release of gas from the emulsion and the relatively low concentration of gas in the carrier, the high partial pressure of gas in the emulsion creates a high driving pressure gradient between the emulsion and gas-poor surfaces.

As a result of the lack of cavitation inception at or near the exit port, a stream of the gas-supersaturated emulsion can be used to rapidly and efficiently enrich a gas-deprived site such as a liquid by convection of the emulsion to the gas-deprived site. Enrichment of a gas-deprived liquid with gas by diffusion from the gas phase to the liquid is, by contrast, an extremely slow process.

The lack of bubbles in the effluent additionally permits unimpeded ejection into the gas-depleted site. When the gas-supersaturated emulsion is ejected in an air environment, the lack of cavitation inception at or near the exit port allows the effluent to behave as if it were not supersaturated with gas. That is, the ejected stream remains intact rather than disintegrating into a diffuse spray near the exit port due to the rapid growth of gas nuclei.

The basic steps for forming the gas-supersaturated emulsion (the same method applies to the formation of a gas-supersaturated suspension) are: preparing the emulsion; exposing the emulsion to a gas at a pressure greater than 2 bar; and delivering the emulsion to a gas-depleted environment at ambient pressure. Typically, the emulsion is exposed to the gas (the primary gas of interest is oxygen) at a pressure of between about 5 bar and about 20 bar. The emulsion could be rapidly mixed (at about 1600 rpm, for instance) for several hours during its exposure to the gas at partial pressures between 100 psi and 1500 psi. Additionally, the emulsion could be delivered to a high pressure hydrostatic pump in order to further increase the partial pressure of the gas.

The emulsion is extruded at the output of a pressurizable vessel through a tube, which delivers the emulsion to the outside environment at between about 0.1 and about 10 ml per minute.

This type of emulsion can be used to efficiently deliver oxygen to the skin, to wounds, or to other environments. In a biological context, the high level of oxygen achieved in such tissues by contact of the emulsion with the tissues should be helpful in a variety of ways, such as collagen synthesis, inhibition of anaerobic bacterial growth, and promotion of aerobic metabolism. A supersaturated oxygen emulsion can also be used to oxygenate blood for a variety of medical applications. The emulsion is injected directly into the bloodstream, thereby increasing oxygen delivery to the blood.

DETAILED DESCRIPTION OF THE PREFERRED EMBODIMENT

Forming the Emulsion:

To form an emulsion, a liquid which will be suspended as droplets within a carrier as well as the carrier must be chosen. The carrier for the emulsion includes any liquid or semi-solid having a relatively low diffusion rate of the gas to be dissolved. The same techniques apply to the formation of a suspension of particles within a liquid carrier.

In general, liquids characterized by high viscosity and low gas solubility are the most effective carriers, since these properties tend to increase the liquid's resistance to bubble formation. Ideally, the viscosity of the carrier should be in the 1 centipoise to 10 centipoise range. Examples of commonly used carriers include glycerin, gels such as hydrogel, VASELINE™ petroleum jelly, paraffin, and waxes.

Gelatins also make effective carriers. For example, 5–10 wt % gelatins were cross-linked in glutaraldehyde to render them insoluble in water, exposed to oxygen at 10–20 bar, and subsequently compressed at high hydrostatic pressures (e.g., 0.5 to 10 kbar) for about an hour. Upon release to hydrostatic pressure of 1 bar, it was noted that no bubbles formed in the gelatin, and a surface $pO_2$>2000 mm Hg was maintained for periods of at least 20–30 minutes.

In contrast to the carrier, the liquid droplets or solid particles which are to be suspended in the carrier must have a high gas solubility. For example, perfluorochemical (PFC) droplets can be suspended within gelatin by adding a hot gelatin solution to a PFC droplet concentrate, mixing briefly, and cooling to affect solidification. With sufficiently high oxygen pressure, the PFC droplets will absorb a high concentration of oxygen and maintain stability at 1 bar by virtue of their small size. Likewise, the gelatin will provide a slow rate of diffusion of oxygen from the particles and through the gelatin to the oxygen-poor site. One such environment that this suspension could be applied to is biologic tissue.

In addition to PFC droplet, other droplet materials that could be used to provide a stable depot of concentrated oxygen include lipids, liposomes, and oils (the class of oils including mineral, coconut, and vegetable oils), most of which have a high solubility of oxygen relative to that of water.

Solid particles useful in preparing suspensions of the present invention are composed of polymers. These polymers have been found to absorb gases such as oxygen under high pressure conditions and to release the gases without bubble formation upon exposure to ambient pressure. The preferred polymers include polyacrylamide (in either its unhydrated or hydrated form), polypropylene, polycarbonate, polyethylene, polylactic acid, polyglycolic acid, polycaprolactone, polyethylene glycol, polystyrene, polysorbate, polymethyl methacrylate and co-polymers thereof. Preferably, the size of the solid particles are within the range of 0.1 to 10 micron.

Any particle or droplet could also be micro or nano-encapsulated with a semi-permeable surface coating that further controls the rate of diffusion from the particle or droplet to the carrier. Encapsulation can be achieved through well-known techniques such as coacervation or vapor deposition.

In order to form an emulsion, one can obtain a commercially available emulsion comprising a desired liquid suspended in water. After centrifuging this emulsion and decanting the supernatant, the desired droplets can be resuspended in a carrier of choice. Likewise, in forming a suspension, one can centrifuge a suspension of particles, decant the supernatant, and resuspend the particles in another carrier of choice.

Preferred Embodiment

The following example is provided to illustrate the above principles. Glycerin was chosen as a carrier because of its low oxygen solubility (0.008 cc $O_2$/g/atm.), relatively high viscosity, and low rate of oxygen diffusion. Moreover, it is a biocompatible liquid, thereby allowing application to the skin or to wounds. Perfluorochemical (PFC) particles were chosen to be suspended in the carrier due to their high oxygen solubility (0.5 cc $O_2$/g/atm.), their inherent ability to form into small particles (typically equal to or less than 0.5 $\mu$m), and their biocompatibility.

In order to prepare the PFC/glycerin suspension, previously prepared commercially available PFC/aqueous suspensions were centrifuged. The PFC particles at the bottom of the centrifuge tubes were resuspended in glycerin after decanting the supernatant.

The PFC/glycerin suspension (200 ml) was placed in a 300 ml capacity Parr reactor vessel, and the suspension was exposed to oxygen at partial pressures as high as 500 to 1500 psi during rapid mixing (at about 1600 rpm) with an impeller stirrer. High oxygen partial pressures were required to drive the oxygen into the suspension over a period of many hours because of the slow rate of diffusion of oxygen through the glycerin.

Despite the high oxygen partial pressures, the oxygen partial pressure developed in the suspension after the above treatment and overnight exposure to oxygen at 300 psi (without stirring) was estimated to be approximately 10 atm. After delivery of the suspension to a Haskel high pressure hydrostatic pump at 1000 psi oxygen partial pressure, the hydrostatic pressure increased to 12,000 psi. At the output of the pump, a 0.009 inch i.d. stainless steel tube—about 100 cm long—was used to deliver the suspension to the outside ambient environment at a flow rate of about 0.2 ml/min.

No bubbles formed in the suspension after extrusion of the suspension into a glass beaker, plastic test tube, or skin (including manual spreading of the suspension on the skin of a hand).

However, the $pO_2$ in the suspension was approximately 10 times higher than that noted in glycerin that had been exposed only to air, as determined with a polarographic type membrane $pO_2$ electrode (manufactured by Diamond General, Ann Arbor). Aliquots of 1 ml of the suspension were in communication with a column of mercury for measuring volume changes at 1 bar as well as in contact with a prototype titanium probe (distal end of which contacted the upper portion of the liquid sample). The probe was seated within the pipette by means of a collar that had been built into the device at its node and glued into the inside of a tube that communicated with the pipette. The probe, driven by a 1500 watt amplifier (manufactured by Sonics and Materials, Inc.), was used to degas the liquid sample during 1 minute periods of sonication.

It was found that the suspension contained approximately 1 ml $O_2$/g. Since the suspension ordinarily contains about 0.1 ml $O_2$/g/bar in water, and the percent volume of PFC in glycerin is similar to that in water, the partial pressure of the gas must have been about 10 bars.

In order to determine how long the suspension retained the high oxygen concentration, the measurement of the oxygen concentration was repeated at 5, 10, 20, and 30 minutes after delivery of the suspension into a 50 ml beaker. Over the first 10 minutes, only 30% of the oxygen was lost from the suspension; however, by 30 minutes, most of the oxygen had diffused out. Thus, it is apparent that the diffusion of oxygen from the suspension is quite slow, partly as a result of the relatively impermeable nature of the carrier.

Dispensing the emulsion:

A simple dispenser for the oxygen-rich cream emulsion can consist of a syringe type design, with the barrel driven by manual rotation of a piston that advances as a screw on threads, similar to the operation of commercially available "indeflators" used to pressurize high pressure balloons (as high as 300 psi) on angioplasty catheters.

Manual compression to at least 300 psi is easily achievable, and a valve at the distal end of the syringe would allow the cream to be squeezed from the syringe in a controlled manner. After dispensing a desired amount of cream, the stopcock would be closed and additional pressure applied to maintain a hydrostatic pressure that equals or exceeds the dissolved gas partial pressure. The syringe would be fabricated from materials that are impermeable to oxygen.

It should be noted that there are a wide variety of geometries which could be employed at or near the exit port(s) which would permit the ejection of the cavitation-free, gas-supersaturated emulsion into a 1 bar environment from a high pressure reservoir. For example, I have found that a 50 micron diameter square borosilicate glass tubing works as effectively as both a round glass tubing and a round stainless steel tubing of similar diameter for this purpose. A rectangular or slit-like geometry characterizing the delivery channels would also be expected to be effective.

Although the present invention has been described and illustrated in detail, it is clearly understood that the same is by way of illustration and example only and is not to be taken by way of limitation, the spirit and scope of the present invention being limited only by the terms of the appended claims.

All references cited in the present specification are incorporated by reference.

What is claimed is:

1. A method of delivering gas into a gas-depleted environment, comprising the steps of:
   a. emulsifying a first liquid having a solubility for a gas higher than the solubility of a second liquid for the gas, the second liquid being immiscible and having a solubility for the gas lower than that of the first liquid;
   b. exposing the emulsion formed in step (a) to the gas at a pressure of greater than 2 bar to form a gas-supersaturated emulsion; and
   c. delivering the gas-supersaturated emulsion to a gas-depleted environment at or near ambient pressure, thereby delivering the gas to the gas-depleted environment.

2. The method of claim 1 wherein the emulsion is exposed to the gas at a pressure of between about 5 bar and about 20 bar.

3. The method of claim 1 wherein the gas is oxygen.

4. The method of claim 1 wherein the first liquid is obtained by centrifuging an aqueous emulsion comprising the first liquid as the internal phase under conditions wherein the internal and external phases separate from one another, and removing the external phase.

5. The method of claim 1 wherein in step b. the gas is dissolved in the emulsion by exposing the emulsion to the gas for several hours during rapid mixing.

6. The method of claim 1 wherein in step b. oxygen is dissolved in the emulsion by exposing the emulsion to oxygen at partial pressures between about 100 psi and about 1500 psi during mixing.

7. The method of claim 1 wherein after step b. and before step c. the gas-supersaturated emulsion is delivered to a high pressure hydrostatic pump in order to further increase the partial pressure of the gas in the gas-supersaturated emulsion.

8. The method of claim 1 wherein step c. comprises extruding the gas-supersaturated emulsion at the output of a pressurized vessel through a tube, which delivers the gas-supersaturated emulsion to the outside environment at between about 0.1 and about 10 ml per minute.

9. The method of claim 1, wherein the gas is selected from the group consisting of oxygen, nitrogen and carbon dioxide.

10. The method of claim 1, wherein the first liquid is selected from the group consisting of perfluorochemicals, lipids and oils.

11. The method of claim 1, wherein the second liquid is selected from the group consisting of glycerin, hydrogel, petroleum jelly, paraffin, waxes and gelatins.

12. The method of claim 1, wherein the gas is oxygen, the first liquid is a perfluorochemical and the second liquid is glycerin.

13. The method of claim 1, wherein the second liquid has a viscosity in the range of about 1 to 10 centipoise.

14. A method of delivering a gas to a gas-depleted environment, comprising the steps of:
   a. providing a gas-supersaturated emulsion comprising a first liquid having a solubility for a gas higher than the solubility of a second liquid for the gas, the first liquid being suspended in fine droplets within the second liquid, the second liquid being immiscible and having a solubility for the gas lower than that of the first liquid, wherein the first liquid is supersaturated with the gas; and b. delivering the gas-supersaturated emulsion to a gas-depleted environment at or near ambient pressure, thereby delivering the gas to the gas-depleted environment.

15. The method of claim 14 wherein the fine droplets are between about 0.1 micron and about 10 microns in diameter.

16. The method of claim 14 wherein the first liquid is a perfluorochemical.

17. The method of claim 14 wherein the first liquid is a lipid or liposome.

18. The method of claim 14 wherein the first liquid is an oil.

19. The method of claim 18 wherein the oil is a mineral, coconut, or vegetable oil.

20. The method of claim 14 wherein the second liquid is glycerin.

21. The method of claim 14 wherein the second liquid is a gel.

22. The method of claim 14 wherein the second liquid is petroleum jelly, paraffin, or wax.

23. The method of claim 14 wherein the second liquid is a 5–10 wt % gelatin which has been cross-linked.

24. The method of claim 14 wherein the first liquid is a perfluorochemical and the second liquid is gelatin.

25. The method of claim 14 wherein the gas is oxygen.

26. The method of claim 14, wherein the gas is selected from the group consisting of oxygen, nitrogen and carbon dioxide.

27. A method of delivering gas into a gas-depleted environment, said method comprising the steps of:

a. preparing an emulsion comprising a first liquid having a solubility for a gas higher than the solubility of a second liquid for the gas, the first liquid being suspended in fine droplets within the second liquid, the second liquid being immiscible and having a solubility for the gas lower than that of the first liquid;

b. exposing the emulsion to the gas at a pressure greater than 2 bar to form a gas-supersaturated emulsion; and c. delivering the gas-supersaturated emulsion through a tube to the gas-depleted environment at or near ambient pressure.

28. A method of delivering oxygen to biologic tissues, comprising the steps of:

a. preparing an emulsion comprising perfluorochemical droplets suspended in glycerin;

b. exposing the emulsion to oxygen at a pressure greater than 2 bar to form an oxygen-supersaturated emulsion; and c. extruding the oxygen-supersaturated emulsion onto the biologic tissues.

* * * * *